United States Patent
Nakajima et al.

(10) Patent No.: US 10,245,011 B2
(45) Date of Patent: Apr. 2, 2019

(54) HEMOSTATIC AGENT APPLICATOR

(71) Applicants: FUSO PHARMACEUTICAL INDUSTRIES, LTD., Osaka (JP); OSAKA UNIVERSITY, Osaka (JP)

(72) Inventors: Kiyokazu Nakajima, Osaka (JP); Keiichi Yamamoto, Osaka (JP)

(73) Assignees: OSAKA UNIVERSITY, Osaka (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 280 days.

(21) Appl. No.: 14/655,346

(22) PCT Filed: Nov. 21, 2013

(86) PCT No.: PCT/JP2013/081439
§ 371 (c)(1),
(2) Date: Jun. 25, 2015

(87) PCT Pub. No.: WO2014/103581
PCT Pub. Date: Jul. 3, 2014

(65) Prior Publication Data
US 2016/0000418 A1     Jan. 7, 2016

(30) Foreign Application Priority Data
Dec. 25, 2012  (JP) ................... 2012-281494

(51) Int. Cl.
*A61B 17/00* (2006.01)
*A61M 35/00* (2006.01)
(Continued)

(52) U.S. Cl.
CPC ....... *A61B 17/00491* (2013.01); *A61M 35/00* (2013.01); *A61M 39/22* (2013.01);
(Continued)

(58) Field of Classification Search
CPC ... A61B 17/00491; A61B 2017/12004; A61M 5/178; A61M 39/0208; A61M 1/0088; A61M 1/009
See application file for complete search history.

(56) References Cited

U.S. PATENT DOCUMENTS 5,267,966 A * 12/1993 Paul ................. A61M 39/0606
137/845
6,334,865 B1    1/2002 Redmond et al.
(Continued)

FOREIGN PATENT DOCUMENTS

DE    202004011036 U1    3/2005
GB         2410707 A     8/2005
(Continued)

OTHER PUBLICATIONS

Extended European Search Report in EP Application No. 13867032.8 dated Sep. 6, 2016, 7 pages.
(Continued)

*Primary Examiner* — Ashley L Fishback
(74) *Attorney, Agent, or Firm* — Marshall, Gerstein & Borun LLP (57) ABSTRACT

Disclosed is a hemostatic agent applicator capable of effectively placing a fluid hemostatic agent on an incision surface. The present invention is a hemostatic agent applicator for use in disposing a fluid hemostatic agent, including a tool body in which a hollow part surrounded by a wall part is formed and which includes an open end part on a downstream side of the wall part, and an inlet provided to a portion of the wall part of the tool body to communicate with the hollow part. This hemostatic agent applicator is useful in medical settings relating to surgical procedures, particularly for surface bleeding of a liver and internal organ surgery such as a spleen and fibroid enucleation. An applicator
(Continued)

further reduced in size can be applied not only in abdominal surgery, but in endoscopic surgery as well.

3 Claims, 8 Drawing Sheets

(51) Int. Cl.
*A61M 39/22* (2006.01)
*A61B 17/132* (2006.01)
*A61B 17/12* (2006.01)

(52) U.S. Cl.
CPC ... *A61B 17/132* (2013.01); *A61B 2017/00544* (2013.01); *A61B 2017/12004* (2013.01); *A61M 2039/229* (2013.01)

(56) References Cited

U.S. PATENT DOCUMENTS

| | | | |
|---|---|---|---|
| 7,615,036 B2* | 11/2009 | Joshi | A61M 1/0088 602/42 |
| 2002/0006429 A1 | 1/2002 | Redmond et al. | |
| 2002/0026215 A1 | 2/2002 | Redmond et al. | |
| 2004/0049158 A1* | 3/2004 | Ley | A61M 39/0613 604/167.03 |
| 2004/0162578 A1 | 8/2004 | Redmond et al. | |
| 2005/0148913 A1* | 7/2005 | Weston | A61M 1/0088 602/2 |
| 2007/0045272 A1* | 3/2007 | French | A61M 5/44 219/216 |
| 2007/0087061 A1 | 4/2007 | Drake et al. | |
| 2007/0203062 A1 | 8/2007 | Ellis-Behnke et al. | |
| 2009/0111734 A1 | 4/2009 | Ellis-Behnke et al. | |
| 2010/0298866 A1 | 11/2010 | Fischvogt | |
| 2011/0004168 A1* | 1/2011 | Eriksson | A61M 1/0088 604/290 |
| 2011/0015585 A1* | 1/2011 | Svedman | A61M 1/0037 604/290 |
| 2011/0092918 A1 | 4/2011 | Jensen et al. | |
| 2011/0201541 A1 | 8/2011 | Takamura et al. | |
| 2012/0070470 A1 | 3/2012 | Pahari et al. | |
| 2012/0209216 A1 | 8/2012 | Jensen et al. | |
| 2012/0296266 A1 | 11/2012 | Malinski | |
| 2013/0303975 A1* | 11/2013 | Gvodas, Jr. | A61M 35/00 604/23 |
| 2014/0038909 A1 | 2/2014 | Takamura et al. | |
| 2015/0073390 A1 | 3/2015 | Jensen et al. | |

FOREIGN PATENT DOCUMENTS

| | | |
|---|---|---|
| JP | 2001-314479 | 11/2001 |
| JP | 2002-272749 | 9/2002 |
| JP | 2003-535658 A | 12/2003 |
| JP | 2004-091003 A | 3/2004 |
| JP | 2008-539257 A | 11/2008 |
| JP | 2010-269140 | 12/2010 |
| JP | 2011-168623 A | 9/2011 |
| WO | WO-2008/048461 A2 | 4/2008 |
| WO | WO-2010/041636 A1 | 4/2010 |
| WO | WO-2011/047753 A1 | 4/2011 |

OTHER PUBLICATIONS

International Search Report in International Application No. PCT/JP2013/081439 dated Feb. 18, 2014, 1 page.

International Preliminary Report on Patentability and Written Opinion in International Application No. PCT/JP2013/081439 dated Jun. 30, 2015, 4 pages.

Office Action in JP application No. 2014-554251 dated Oct. 24, 2017, 7 pages.

\* cited by examiner

HEMOSTATIC AGENT APPLICATOR

TECHNICAL FIELD

The present invention relates to a hemostatic agent applicator and, more specifically, to a hemostatic agent applicator capable of effectively disposing a hemostatic agent such as a gelatinous hemostatic agent which is used during surgery on a bleeding surface to stop the bleeding.

BACKGROUND ART

A hemostatic agent (material) for a living body and a biomedical adhesive (material) have been widely used as medicinal supplies or medical equipment in surgical operations, and the usefulness thereof has been established. However, such materials contain components derived from a living body, and thus need to be handled as carefully as a blood product is handled in terms of infectiousness.

A non-living body-derived hemostatic agent that contains complete chemosynthesis peptide as a component has been developed (Patent Literature 1 to 3). The non-living body-derived hemostatic agent is useful in terms of avoiding infection when compared to a living body-derived product, and a clinical application thereof has been carried out. As an example, the non-living body-derived hemostatic agent is composed of peptide which includes three types of amino acids (arginine, alanine and aspartic acid). When an aqueous solution having the same agent is topically applied to an incision surface during surgery, peptides automatically and regularly form an aggregate, and rapidly form a nanofiber to gelate. In this way, a structure similar to that of a component of a living body such as collagen, and fibrin is generated. As a result, hemostatic effect is exhibited on the incision surface.

The non-living body-derived hemostatic agent is considered useful for stopping the bleeding of a deep part of a living body, in particular, an incision surface of a parenchymatous organ and the like which may not be achieved by existing hemostasis means (for example, compression, ligation, and electrocoagulation). On the other hand, the agent has a property of gel during application, and thus there is a problem that the agent is applied to an incision surface which is not horizontal. The problem occurs since there is concern that the applied gel may flow out of the incision surface due to gravity. In addition, a non-living body-derived hemostatic agent containing power is known (Patent Literature 4). However, the hemostatic agent containing power has a problem in that power scatters when the hemostatic agent is applied, thereby obstructing the field of vision.

CITATION LIST

Patent Literature

Patent Literature 1: International Publication Pamphlet No. WO 2010/041636
Patent Literature 2: Japanese National Publication of International Patent Application No. 2008-539257
Patent Literature 3: Japanese National Publication of International Patent Application No. 2011-168623
Patent Literature 4: International Publication Pamphlet No. WO 2008/048461

SUMMARY OF INVENTION

Technical Problem

The invention has been conceived to solve the above-mentioned problem, and an object of the invention is to provide a hemostatic agent applicator capable of effectively applying a hemostatic agent to an incision surface by preventing the hemostatic agent from flowing out due to gravity irrespective of whether the incision surface is in a horizontal state during surgery when a hemostatic agent having fluidity such as a gelatinous hemostatic agent is used as the hemostatic agent. Another object of the invention is to provide a hemostatic agent applicator capable of preventing a hemostatic agent from scattering when the hemostatic agent composed of powder is used.

Solution to Problem

The invention corresponds to a hemostatic agent applicator for use in disposing a fluid hemostatic agent, the applicator including a tool body in which a hollow part surrounded by a wall part is formed and which includes an open end part on a downstream side of the wall part, and an inlet provided to a portion of the wall part of the tool body to communicate with the hollow part.

In one embodiment, an inside of the wall part has a tapered shape arranged to be open toward a side of the open end part of the tool body.

In one embodiment, a distal end of the open end part is provided with a skirt along a circumference direction of the tool body.

In one embodiment, the inlet is provided on an upstream side of the tool body.

In one embodiment, the inlet is provided with a T shape stopcock.

In one embodiment, the wall part is provided with an outlet which communicates with the hollow part.

In one embodiment, the open end part is capable of coming into close contact with an incision surface formed during surgery.

Advantageous Effect of Invention

According to the invention, it is possible to efficiently dispose a fluid hemostatic agent on an incision surface by preventing the fluid hemostatic agent from flowing out after application. As a result, it is possible to more effectively achieve hemostasis on the incision surface while more reducing the amount of used hemostatic agent. A hemostatic agent applicator of the invention has a relatively simple configuration, and thus there is no need to go through a complicated manufacturing process. As a result, it is possible to provide the hemostatic agent applicator as a disposable device for hemostasis while suppressing manufacturing cost. Thus, the risk of contracting an undesired infectious disease can be avoided in advance by using the applicator.

BRIEF DESCRIPTION OF DRAWINGS

FIGS. 3A to 3C are schematic diagrams for description of a method of stopping the bleeding of a crushed tissue occurring on an incision surface during surgery using the hemostatic agent applicator of the invention illustrated in FIG. 1, in which

FIGS. 5A and 5B are schematic diagrams for description of a method of stopping the bleeding of a crushed tissue occurring on an incision surface during surgery using the hemostatic agent applicator of the invention illustrated in FIG. 4, in which

FIGS. 7A and 7B are schematic diagrams for description of a method of stopping the bleeding of a crushed tissue occurring on an incision surface during surgery using the hemostatic agent applicator of the invention illustrated in FIG. 6, in which

FIGS. 9A and 9B are cross-sectional views of the hemostatic agent applicator of the invention illustrated in FIG. 8 for description of an example of a connection mode of a skirt in the hemostatic agent applicator, in which

DESCRIPTION OF EMBODIMENT

Hereinafter, the invention will be described in detail with reference to the drawings.

Figure 1:
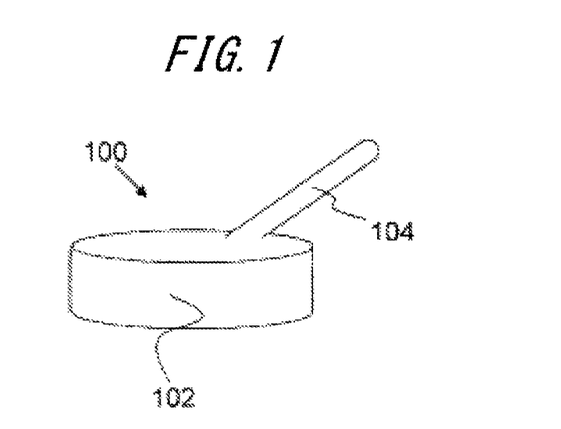
FIG. 1 is a perspective view schematically illustrating and describing a hemostatic agent applicator according to an embodiment of the invention.

FIG. 1 is a perspective view schematically illustrating and describing a hemostatic agent applicator according to an embodiment of the invention.

A hemostatic agent applicator 100 of the invention includes a tool body 102 and an inlet 104 connected to the tool body 102. Referring to FIG. 1, for example, the tool body 102 has a shape of a frying pan, that is, a cylindrical shape or a substantially cylindrical shape in which one base is closed and the other base is opened. In the invention, the shape is not particularly limited thereto. Referring to a size of the tool body 102 of FIG. 1, a diameter at least on a side of the open base is in a range, for example, from 1 cm to 5 cm, preferably, from 1.5 to 2.5 cm, and a height is in a range, for example, from 0.5 cm to 1 cm, preferably from 0.6 cm to 0.8 cm. In an employed size, an incision surface may be covered during surgery described below. Referring to FIG. 1, the inlet 104 is provided to be inclined at a certain angle on an upper surface portion of the tool body 102 (that is, an upstream portion with respect to an open end part described below). Alternatively, in the invention, the inlet 104 may be provided on a lateral surface portion of the body 102.

As described above, even though the body 102 illustrated in FIG. 1 has the shape of the frying pan, and thus the bases have circular shapes or substantially circular shapes, the invention is not limited to the shapes. It is possible to form an arbitrary shape (for example, an ellipse, a quadrangle such as a rectangle or a square, and a triangle) according to ease of use for a doctor who performs surgery or a shape of an incision surface described below. For example, the hemostatic agent applicator of the invention is used during surgery by a doctor who performs the surgery. Thus, the applicator preferably has a size such that the applicator is held by one hand and preferably has an external shape such that the applicator is easily gripped.

Figure 2:
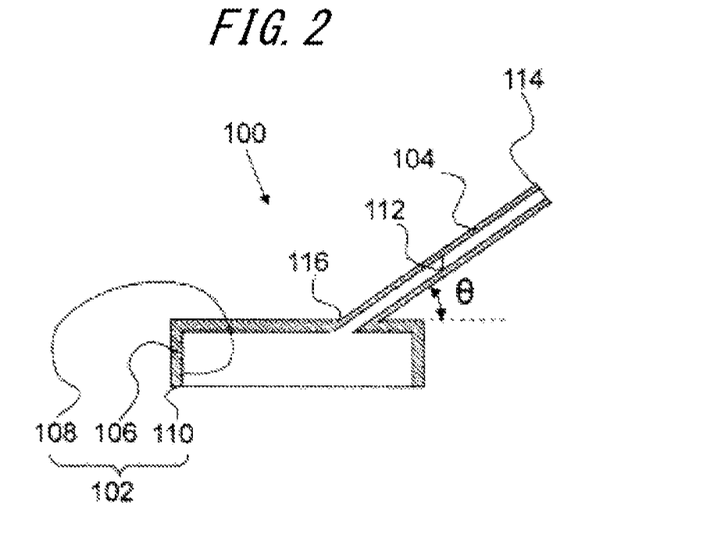
FIG. 2 is a cross-sectional view of the hemostatic agent applicator of the invention illustrated in FIG. 1.

FIG. 2 is a cross-sectional view of the hemostatic agent applicator of the invention illustrated in FIG. 1.

As illustrated in FIG. 2, the tool body 102 is surrounded by a closed base and a wall part 106 provided to have a certain thickness on a lateral surface, and an inside thereof forms a hollow part 108. Further, the tool body 102 has an open end part 110 in a lower part (on a downstream side) of the wall part 106, and an open end including the open end part 110 communicates with the hollow part 108. An installation surface of the open end part 110 is preferably subjected to rounding processing such that the open end part 110 is atraumatic with respect to contact with the incision surface described below.

A shape of the hollow part 108 may not be identical to an external shape of the tool body 102. However, the hollow part 108 has a cylindrical shape in FIG. 2. For example, the hollow part 108 has an internal diameter in a range from 1.3 cm to 2.3 cm. The internal diameter is employed such that the incision surface is covered during surgery described below.

In addition, the hollow part 108 of the tool body 102 communicates with an internal pipe 112 of the inlet 104 connected to the tool body 102. An axis length of the inlet 104 is not particularly limited. For example, the axis length may be in a range from 1 cm to 5 cm. An internal diameter of the inlet 104 is not particularly limited. For example, the internal diameter may be in a range from 0.3 cm to 0.6 cm. An end part 114 of the inlet 104 is connected to another device (not illustrated) such that the end part 114 comes into contact with a syringe containing a fluid hemostatic agent directly or through a medical tube. To reliably connect the end part 114 to the other device, the end part 114 of the inlet 104 may be provided with a known falling prevention means such as a luer lock.

Further, an angle θ between the inlet 104 and an upper surface of the tool body 102 is not particularly limited, and may be set in consideration of ease of gripping for a doctor using the applicator. Examples of the angle θ may include an angle from 20° to 80°.

Referring to FIGS. 1 and 2, the tool body 102 and the inlet 104 are formed as a single piece. However, the invention is not limited to the single piece form. In other words, the tool body 102 and the inlet 104 may be separately formed and connected to each other by being bonded to each other through a connecting part 116 or such that insides thereof communicate with each other by screwing and the like. In addition, the tool body 102 and the inlet 104 may be connected to each other through a variable angle type adapter (not illustrated).

The hemostatic agent applicator of the invention is made of a material such as plastic, and metal. Plastic generally used for medical instruments such as polypropylene, polyethylene, poly(meth)acrylate, polycarbonate, and a copolymer thereof exemplifies the plastic used for the hemostatic agent applicator. The applicator is preferably transparent since an inside is observable when the bleeding is stopped if the applicator is transparent. Stainless steel and titanium exemplify the metal used for the hemostatic agent applicator.

In the present invention, the tool body 102 and the inlet 104 may not necessarily be formed of using the same material. For example, the tool body 102 may be formed of plastic such as polypropylene, and the inlet 104 may be formed of metal such as stainless steel. Further, in the invention, insides of the tool body 102 and the inlet 104 (that is, the hollow part and the internal pipe) may be subjected to predetermined coating for preventing the fluid hemostatic agent from being attached thereto and remaining. Hydrophilic coating exemplifies the predetermined coating.

Referring to FIG. 2, the fluid hemostatic agent is introduced to the hemostatic agent applicator 100 of the invention from the end part 114 of the inlet 104.

The fluid hemostatic agent usable in the hemostatic agent applicator of the invention is a hemostatic agent having a property of gel or liquid. When the hemostatic agent is disposed on the incision surface during the surgery, the hemostatic agent is expected to easily infiltrate into a crushed tissue due to fluidity and permeate through a fractured blood vessel. However, when the incision surface is in a horizontal direction during the surgery, that is, when the incision surface is formed in a vertical direction or formed at an arbitrary angle, there is concern that the hemostatic agent easily flows out before infiltrating into the crushed tissue. The hemostatic agent applicator of the invention may appropriately provide the hemostatic agent to the crushed tissue by preventing the fluid hemostatic agent from flowing out. Further, the hemostatic agent applicator of the invention may be used for a hemostatic agent having a property of powder. A powdery hemostatic agent may have a risk of scattering and obstructing a surgical field when being applied. The hemostatic agent applicator of the invention may prevent the fluid hemostatic agent containing powder from scattering and ensure a clear surgical field.

It is preferable to use a gelatinous or liquid hemostatic agent manufactured using a material which is not derived from a living body as the fluid hemostatic agent available for the hemostatic agent applicator of the invention in order to avoid infection of an undesired infectious disease. The non-living body-derived hemostatic agent is not particularly limited. Hemostatic agents containing self-assembly peptide as described in International Publication Pamphlet No. 2010/041636 (Patent Literature 1), Japanese National Publication of International Patent Application No. 2008-539257 (Patent Literature 2) and Japanese National Publication of International Patent Application No. 2011-168623 (Patent Literature 3), and a powder hemostatic agent derived from starch as described in International Publication Pamphlet No. 2008/048461 (Patent Literature 4) exemplify the non-living body-derived hemostatic agent.

Next, a description will be given of a method of stopping the bleeding on the incision surface during the surgery using the hemostatic agent applicator 100 of the invention.

Figure 3A:
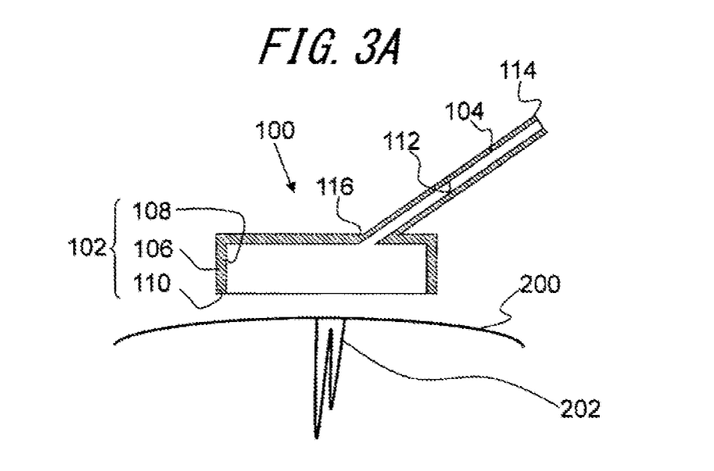
FIG. 3A is a diagram for description of an appearance in which the hemostatic agent applicator of the invention is disposed on the crushed tissue.

As illustrated in FIG. 3A, a hemostatic agent applicator 100 of the invention is disposed to completely cover a crushed tissue 202 in an incision surface 200 formed during the surgery. Specifically, the crushed tissue 202 is covered with a tool body 106 of the applicator 100. In this instance, the incision surface 200 and an open end part 110 of a tool body 102 are close to each other. Further, the end part 114 of the inlet 104 is previously connected to a syringe (not illustrated), and the like. In this way, a sealed space is formed among the incision surface 200, the hollow part 108 of the tool body 102, and the internal pipe 112 of the inlet 104. Due to the sealed space, bleeding from the crushed tissue 202 is pressurized by air pressure and temporarily suppressed.

Figure 3B:
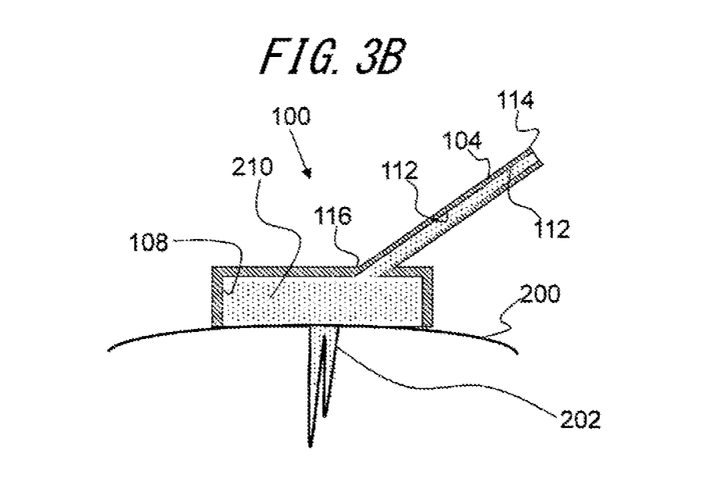
FIG. 3B is a diagram for description of an appearance in which a fluid hemostatic agent is introduced to the tissue through the disposed hemostatic agent applicator.

Subsequently, as illustrated in FIG. 3B, a fluid hemostatic agent 210 is introduced from the end part 114 of the inlet 104. The fluid hemostatic agent 210 flows up to the hollow part 108 of the tool body through the internal pipe 112 of the inlet 104, and finally reaches the crushed tissue 202 in the incision surface 200. When the fluid hemostatic agent 210 reaches the crushed tissue 202, it is preferable to slightly incline the applicator 100, provide a slight gap between the incision surface 202 and the open end part 110 of the tool body, and discharge air which is present in the inside diameter pipe 112 and the hollow part 108 to an outside.

After the fluid hemostatic agent 210 reaches up to the crushed tissue 202, a doctor who is in charge of stopping the bleeding may, for example, further press the syringe, thereby applying pressure to the fluid hemostatic agent 210. It is desired that the pressing is performed with an appropriate pressure not to cause the flowing out of the fluid hemostatic agent from the tool body.

In this way, the fluid hemostatic agent 210 may further infiltrate into a deep part of the crushed tissue 202, thereby more heightening an effect of the hemostatic agent in the deep part. In this state, the doctor continuously performs pressing for some time until the bleeding is completely stopped. Referring to FIG. 3B, the sealed space formed among the incision surface 200, the hollow part 108 of the tool body 102, and the internal pipe 112 of the inlet 104 is filled with the fluid hemostatic agent 210, and is pressed by an internal pressure thereof until the bleeding is completely stopped. Further, the fluid hemostatic agent 210 stays in the sealed space, and thus is prevented from flowing out irrespective of whether the incision surface 200 is in a horizontal direction, a vertical direction, or a direction having another angle.

Figure 3C:
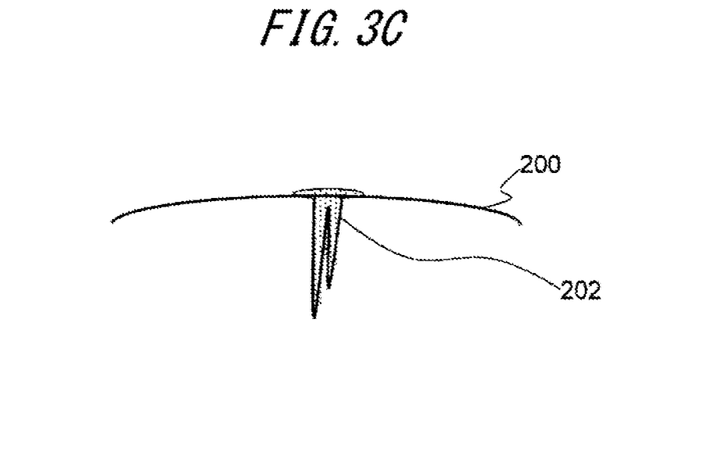
FIG. 3C is a diagram for description of a state of the incision surface after the fluid hemostatic agent is introduced to the incision surface and then the hemostatic agent applicator of the invention is removed.

Finally, after the bleeding from the incision surface is completely stopped, the hemostatic applicator of the invention is removed from the incision surface 200. As a result, the hemostatic agent is applied only to the crushed tissue 202 of the incision surface 200 and the vicinity thereof (FIG. 3C).

In this way, it is possible to stop the bleeding by disposing the fluid hemostatic agent on a desired incision surface without the fluid hemostatic agent being flow out.

Referring to the hemostatic agent applicator of the invention, a description has been given of the method of stopping the bleeding while pressing the sealed space formed among the incision surface 200, the hollow part 108 of the tool body 102, and the internal pipe 112 of the inlet 104 with the internal pressure of the fluid hemostatic agent 210 by increasing the pressure of the syringe until the bleeding is stopped with reference to FIG. 3B. However, the use of the applicator of the invention is not limited to the method. In other words, the end part 114 of the inlet 104 may be provided with a T shape stopcock (not illustrated). Here, one of two remaining parts of the T shape stopcock may be connected to the syringe that contains the fluid hemostatic agent, and the other one may be connected to an empty syringe.

In this case, when a lever of the T shape stopcock is switched after the fluid hemostatic agent 210 is supplied up to the crushed tissue 202 of the incision surface 200, the fluid hemostatic agent filled in the sealed space may be pressed by a pressure of air discharged from the air pump or the empty syringe in place of supply of the fluid hemostatic agent. In this way, it is possible to reduce the amount of the fluid hemostatic agent used to stop the bleeding.

Figure 4:
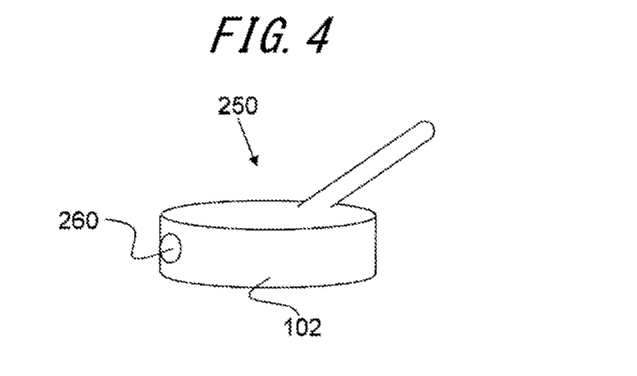
FIG. 4 is a perspective view schematically illustrating and describing a hemostatic agent applicator according to another embodiment of the invention.

FIG. 4 is a perspective view schematically illustrating and describing a hemostatic agent applicator according to another embodiment of the invention.

A hemostatic agent applicator 250 of the invention illustrated in FIG. 4 is provided with a hole 260 in a part of a lateral surface portion of a tool body 102, and the hole 260 is provided with a bag-like or flexible movable member.

Figure 5A:
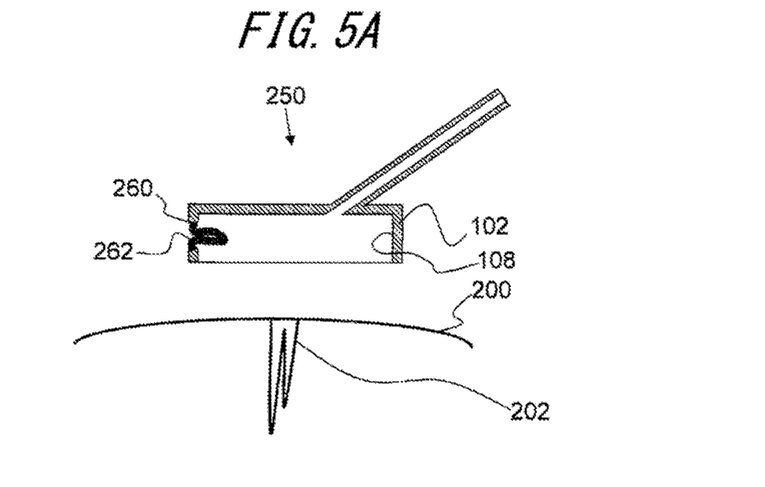
FIG. 5A is a diagram for description of an appearance in which the hemostatic agent applicator of the invention is disposed on the crushed tissue.
Figure 5B:
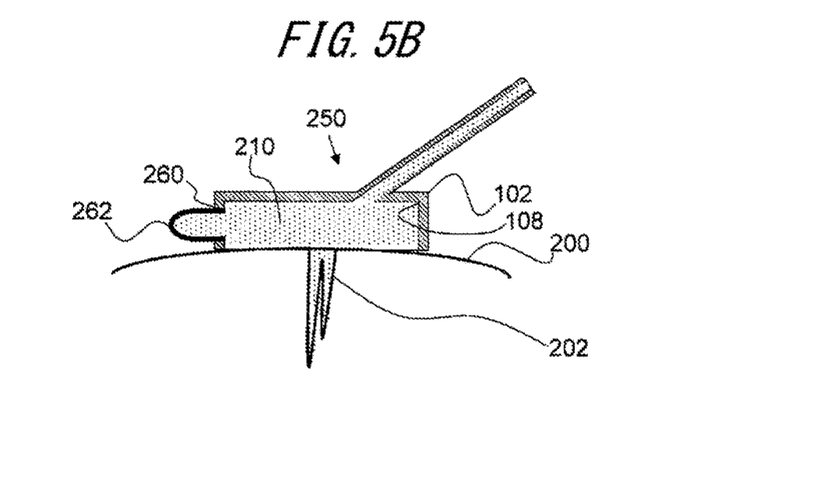
FIG. 5B is a diagram for description of an appearance in which a fluid hemostatic agent is introduced to the tissue through the disposed hemostatic agent applicator.

As illustrated in FIG. 5A, a movable member 262 is accommodated in the hole 260 before the hemostatic applicator 250 of the invention is used. During use, as illustrated in FIG. 5B, when the tool body 102 is filled with the fluid hemostatic agent 210 through an internal pipe 112 of an inlet 104, a hollow part 108 in the tool body 102 is filled with the fluid hemostatic agent 210 together with air in the tool body 102. In addition, according to the amount of the introduced agent, the movable member 262 may protrude outward from the hole 260 to function as a dam FIG. 6 is a perspective view schematically illustrating and describing a hemostatic agent applicator corresponding to another embodiment of the invention.

Figure 6:
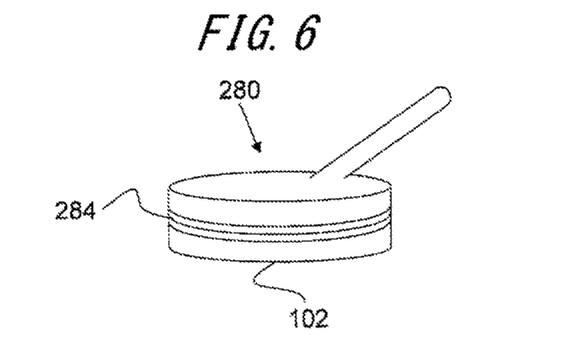
FIG. 6 is a perspective view schematically illustrating and describing a hemostatic agent applicator according to another embodiment of the invention.

A hemostatic agent applicator 280 of the invention illustrated in FIG. 6 is provided with a bellows-shaped member 284 around a lateral surface portion of a tool body 102.

Figure 7A:
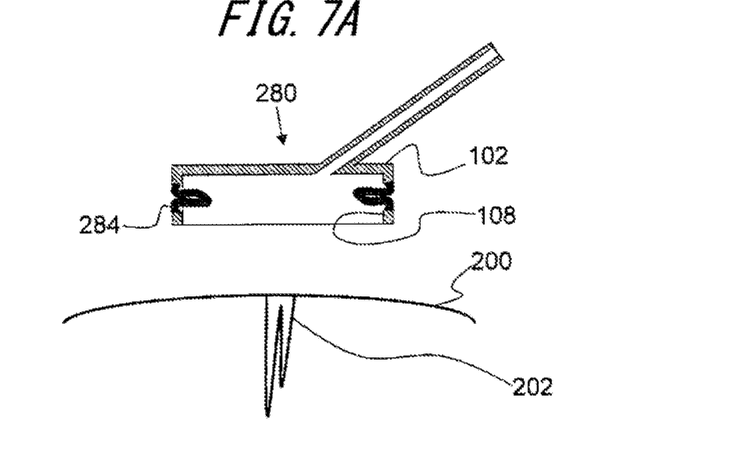
FIG. 7A is a diagram for description of an appearance in which the hemostatic agent applicator of the invention is disposed on the crushed tissue.
Figure 7B:
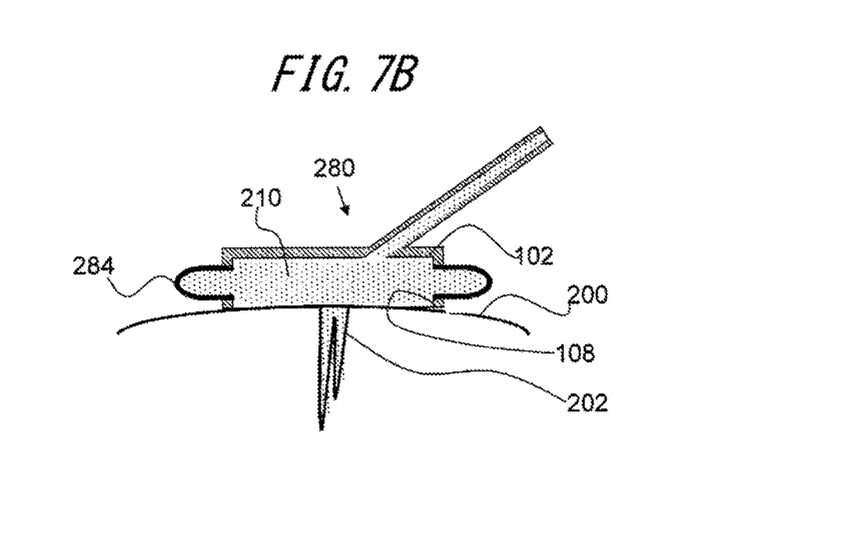
FIG. 7B is a diagram for description of an appearance in which a fluid hemostatic agent is introduced to the tissue through the disposed hemostatic agent applicator.

As illustrated in FIG. 7A, before use of the hemostatic applicator 280 of the invention, the bellows-shaped member 284 is accommodated in the tool body 102. During use, as illustrated in FIG. 7B, when the tool body 102 is filled with the fluid hemostatic agent 210 through an internal pipe 112 of an inlet 104, a hollow part 108 in the tool body 102 is filled with the fluid hemostatic agent 210 together with air in the tool body 102. In addition, according to the amount of the introduced agent, the bellows-shaped member 284 may protrude outward to function as a damper, and maintain the inside of the tool body 102 under an appropriate pressure.

Figure 8:
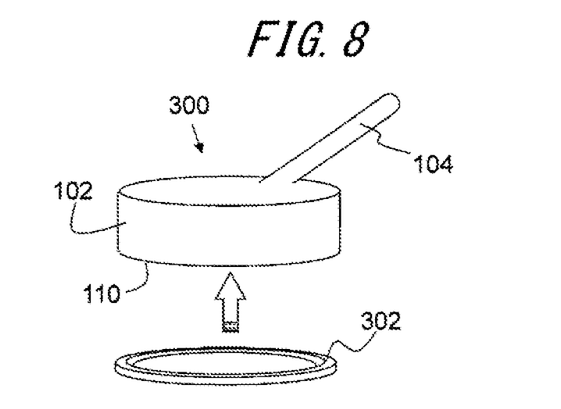
FIG. 8 is an exploded perspective view schematically illustrating and describing a hemostatic agent applicator according to another embodiment of the invention.

FIG. 8 is an exploded perspective view schematically illustrating and describing a hemostatic agent applicator according to another embodiment of the invention.

In the hemostatic agent applicator 300 of the invention illustrated in FIG. 8, a skirt 302 is provided along a circumference direction of a tool body 102 at a distal end of an open end part 110 of the tool body 102.

The skirt 302 is made of a material such as silicone rubber, natural rubber, non-rigid plastic, and the like. When the bleed is stopped, the skirt 302 may come into contact with an incision surface, thereby reducing damage of the incision surface, and further enhancing adhesion between the applicator and the incision surface.

Figure 9A:
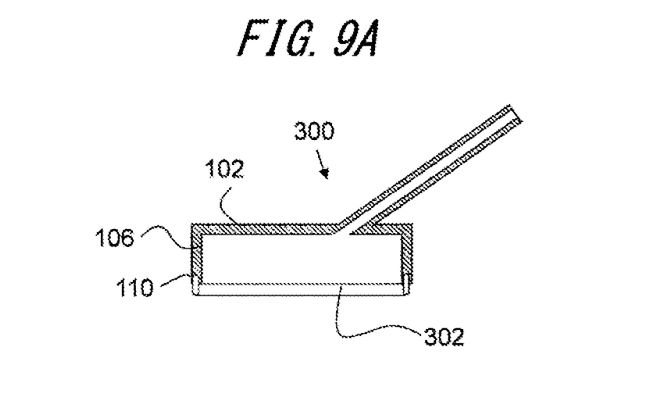
FIG. 9A is a diagram for description of a state in which the skirt is fixed such that a portion thereof is buried in a wall part in an open end part of a tool body.
Figure 9B:
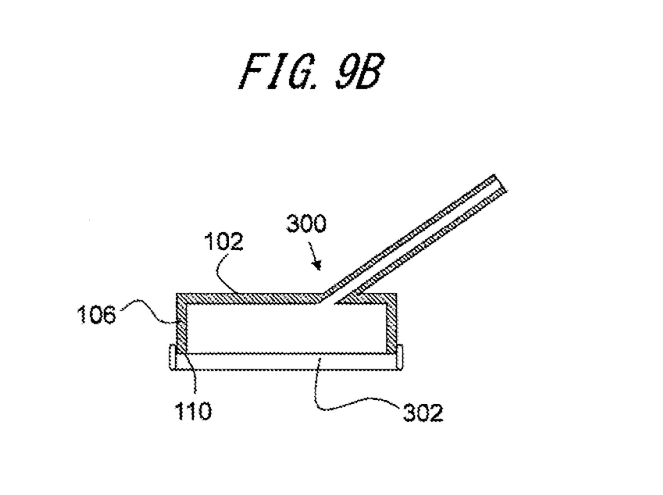
FIG. 9B is a diagram for description of a state in which the skirt is fixed such that a portion thereof surrounds an outer circumference of the open end part of the tool body.

FIGS. 9A and 9B are diagrams for description of an example of a connection mode of the skirt 302 in the hemostatic agent applicator 300 of the invention illustrated in FIG. 8, and is a cross-sectional view of the hemostatic agent applicator 300.

As illustrated in FIG. 9A, in the hemostatic agent applicator 300, the skirt 302 may be fixed such that a portion thereof is buried in a wall part 106 in the open end part 110 of the tool body 102. Alternatively, as illustrated in FIG. 9B, in the hemostatic agent applicator 300, the skirt 302 may be fixed such that a portion thereof surrounds an outer circumference of the open end part 110 of the tool body 102.

Figure 10:
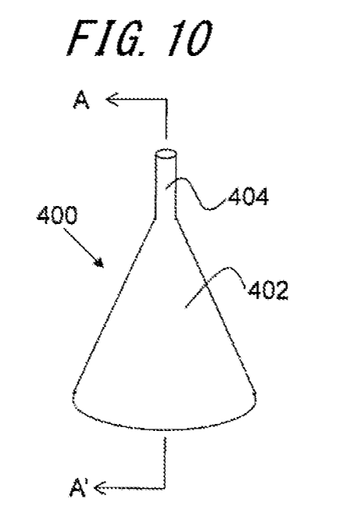
FIG. 10 is a perspective view schematically illustrating and describing a hemostatic agent applicator according to another embodiment of the invention.

FIG. 10 is a perspective view schematically illustrating and describing a hemostatic agent applicator according to another embodiment of the invention.

Referring to FIG. 10, the hemostatic agent applicator 400 of the invention includes a conical tool body 402 in which a base is open, and an inlet 404 connected to a top of the tool body 402. Referring to FIG. 10, the tool body 402 has a shape of a right circular cone. However, the invention is not limited to the shape, and the tool body 402 may have a shape of an oblique circular cone in which an axis is inclined at an arbitrary angle. When the tool body 402 has a tapered shape that extends toward a downstream side, ease of gripping of the applicator is further enhanced.

Figure 11:
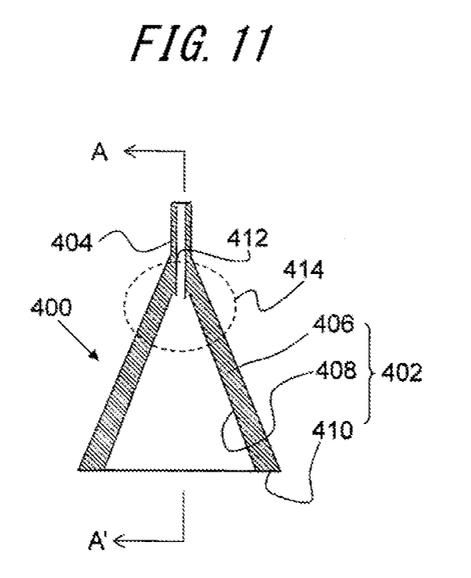
FIG. 11 is a cross-sectional view taken along line A-A' of the hemostatic agent applicator of the invention illustrated in FIG. 10.

FIG. 11 is a cross-sectional view taken along line A-A' of the hemostatic agent applicator of the invention illustrated in FIG. 10.

As illustrated in FIG. 11, the tool body 402 includes a wall part 406 having a certain thickness at a lateral surface, and an inside thereof forms a hollow part 408. Further, the tool body 402 includes an open end part 410 in a lower part (on the downstream side) of the wall part, and an open end including the open end part 410 communicates with the hollow part 408. A shape of the hollow part 408 may not be identical to the external shape of the tool body 402. Referring to FIGS. 7A and 7B, the hollow part 408 has the tapered shape that extends toward the downstream side, and communicates with an internal pipe 412 of the inlet 404 at the top 414 (upstream side).

In the hemostatic agent applicator 400 illustrated in FIG. 11, a hemostatic agent discharged to the hollow part 408 of the tool body 402 through the internal pipe 412 of the inlet 404 uniformly spreads in the hollow part 408. In this way, it is possible to dispose an amount of the hemostatic agent per unit area more constantly on the incision surface.

Figure 12:
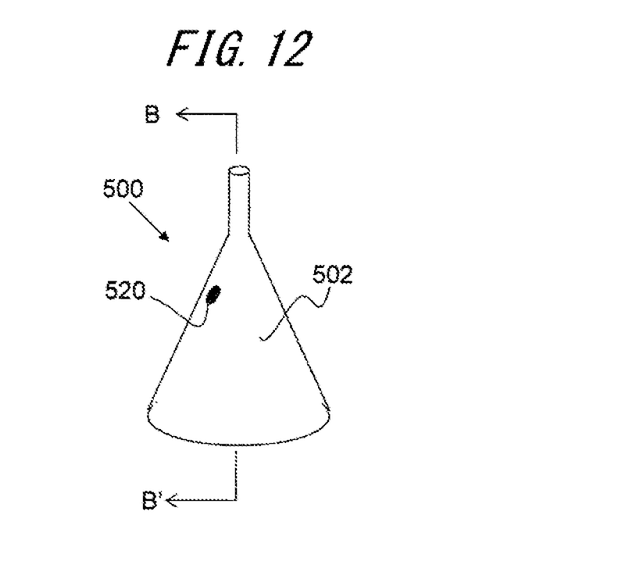
FIG. 12 is a perspective view schematically illustrating and describing a hemostatic agent applicator according to another embodiment of the invention.

FIG. 12 is a perspective view schematically illustrating and describing a hemostatic agent applicator according to another embodiment of the invention.

A hemostatic agent applicator 500 illustrated in FIG. 12 is similar to the applicator 400 illustrated in FIG. 11 except that an outlet 520 is provided in a portion of a lateral surface of a conical tool body 502. A size and a shape of the outlet 520 is not particularly limited if the outlet 520 can be covered with a finger. For example, a diameter is in a range from 1 mm to 3 mm, and examples of the shape may include a circle, an ellipse, or a rectangle. The outlet 520 is preferably provided on an upstream side of the tool body 402 such that a hemostatic agent does not easily flow out of the tool body 402 when the hemostatic agent is introduced.

Figure 13:
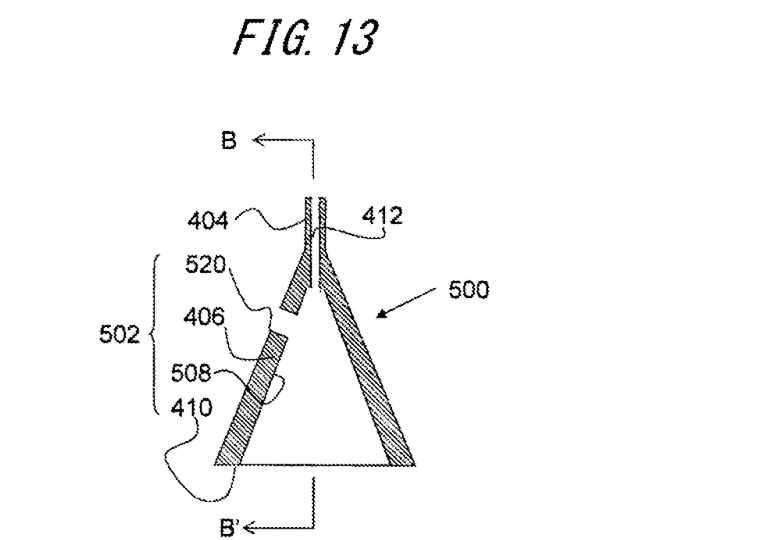
FIG. 13 is a cross-sectional view taken along line B-B' of the hemostatic agent applicator of the invention illustrated in FIG. 12.

FIG. 13 is a cross-sectional view taken along line B-B' of the hemostatic agent applicator of the invention illustrated in FIG. 12.

As illustrated in FIG. 13, the tool body 502 includes a wall part 406 having a certain thickness at a lateral surface, and an inside thereof forms a hollow part 508. Further, the tool body 502 includes an open end part 410 in a lower part (on the downstream side) of the wall part, and an open end including the open end part 410 communicates with the hollow part 508. A shape of the hollow part 508 may not be identical to the external shape of the tool body 502. Referring to FIG. 13, the hollow part 508 has a tapered shape that extends toward the downstream side, and communicates with an internal pipe 412 of the inlet 404 at a top.

Referring to FIG. 13, the outlet 520 communicates with the hollow part 508. The outlet 520 may have a shape of any of a circle, an ellipse, and a rectangle. The size of the outlet 520 is not particularly limited. For example, it is preferable to maintain a size at which the outlet 520 may be sufficiently covered with an index finger.

In the hemostatic agent applicator 500 illustrated in FIG. 13, when a fluid hemostatic agent is introduced through the internal pipe 412 of the inlet 404, the outlet 520 is not pressed with a finger and is opened. As a result, while the fluid hemostatic agent is introduced to the hollow part 508, air which is present therein is discharged through the outlet 520. Thereafter, when a doctor presses the outlet 520 with a finger, a sealed space formed among an incision surface, the hollow part 508 of the tool body 502, and the internal pipe 412 of the inlet 404 is filled with the fluid hemostatic agent. In addition, it is possible to maintain a state in which the sealed space is pressed by an internal pressure thereof until the bleeding is completely stopped. In this way, it is possible to easily discharge unnecessary air which is present in the hollow part 508, and the like to an outside through the outlet 520 when the fluid hemostatic agent is introduced.

The hemostatic agent applicator of the invention has been described for a case having an aspect in which a doctor who performs surgery directly holds the hemostatic agent applicator with a hand to stop the bleeding. However, the invention is not limited to the aspect. In other words, for example, when the hemostatic agent applicator is applied to a distal end part of an endoscope, the hemostatic agent applicator may be used to stop the bleeding from an incision surface in endoscopic surgery.

Figure 14:
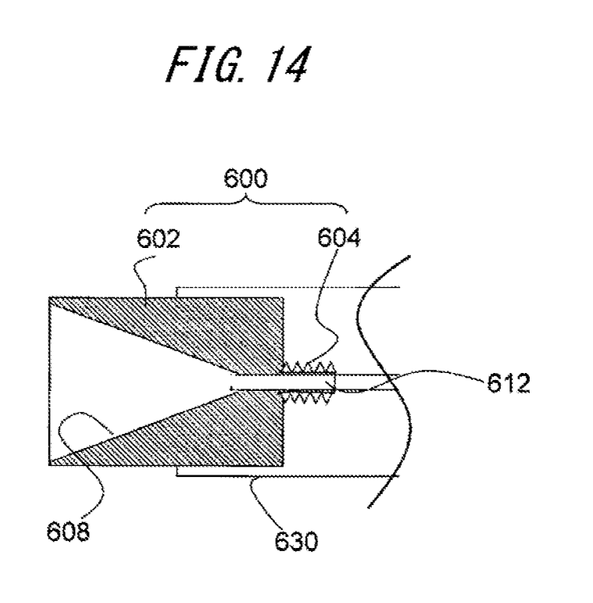
FIG. 14 is a cross-sectional view schematically illustrating and describing a hemostatic agent applicator connected to a distal end part of an endoscope according to another embodiment of the invention.

FIG. 14 is a cross-sectional view schematically illustrating and describing a hemostatic agent applicator connected to a distal end part of an endoscope according to another embodiment of the invention.

As illustrated in FIG. 14, for example, a hemostatic agent applicator 600 of the invention includes a tool body 602 having a cylindrical shape and an inlet 604 connected to one end part of the tool body 602. Referring to FIG. 14, a screw thread is formed on an outer circumference of the inlet 604, and the inlet 604 has a shape fixable to a distal end part of an endoscope 630 by screwing. A fluid hemostatic agent passes through an internal pipe 612 of the inlet 604 through the endoscope, and is disposed on a desired incision surface through a hollow part 608 of the tool body 602. Referring to FIG. 14, the screw thread is formed on the outer circumference of the inlet 604. However, the invention is not limited to this shape. A screw thread may be formed on an outer circumference portion of the tool body 602, and the tool body 602 may be screwed to the distal end part of the endoscope 630.

In this way, it is possible to efficiently apply the fluid hemostatic agent to the incision surface in endoscopic surgery.

Compressing using paper or gauze has been selected to efficiently apply a hemostatic agent to a part. However, with regard to a fluid hemostatic agent, in this scheme, gel flows out to a side (in a horizontal direction) from an incision surface, and essential filling in the incision surface (bleeding surface) is not maintained. In this regard, when the hemostatic agent applicator of the invention is used, it is possible to apply the fluid hemostatic agent to a targeted incision surface without the fluid hemostatic agent flowing out in the horizontal direction. In this way, it is possible to exhibit hemostatic effect of the fluid hemostatic agent at the maximum.

Further, in the invention, it is possible to inject air or inert gas into the hollow part as necessary after the fluid hemostatic agent is introduced. In this way, it is possible to apply a pressing force by atmospheric pressure, and more effectively fill a part with the fluid hemostatic agent.

Furthermore, in a conventional pressing scheme, a pressed region cannot be visually recognized, and hemostatic effect cannot be appropriately confirmed during a surgical operation. However, in the invention, at least a tool body may be configured as a transparent member (for example, plastic), and thus it is possible to stop the bleeding while successively observing each step of stopping the bleeding.

EXAMPLES

Hereinafter, the invention will be described in more detail using Examples. However, the invention is not limited to the embodiments as described in the Examples.

Example 1: Fabrication of a Hemostatic Agent Applicator

The hemostatic agent applicator 100 illustrated in FIGS. 1 and 2 is manufactured as below, for example.

A polypropylene inlet having a length of 20 mm and an internal diameter of 2 mm is attached to a cylindrical tool body, which has a height of 7 mm and an internal diameter of 15 mm and has one open end, made of a transparent polymethylmethacrylate resin using a cyano acrylate adhesive such that the angle θ illustrated in FIG. 2 becomes 45°. Further, a skirt made of a silicone resin is mounted on a side of the open end part of the tool body by tightening. A top plate of the tool body is provided with an outlet having a diameter of 1 mm. In this way, the example of the hemostatic agent applicator 100 illustrated in FIGS. 1 and 2 is manufactured.

Example 2: Hemostasis of an Incision Site of a Rabbit Using a Hemostatic Applicator An abdomen of a rabbit (Japanese white color species) put under general anesthesia is cut open, a liver is exposed, and an incision is made on the surface of the liver using scissors. The incision site is maintained at inclined angles of 0°, about 30°, and about 60°, and the skirt of the applicator fabricated in Example 1 is closely pressed against an affected part. In this state, the space of the tool body is filled with a fluid hemostatic agent (about 1 mL) manufactured by a method disclosed in Patent Literature 1 through the inlet of the applicator, and the pressed state is maintained for two minutes. Thereafter, the applicator is removed, and whether the fluid hemostatic agent flows out is verified while the inclination of the incision site is maintained. Based on whether the fluid hemostatic agent flows out, hemostatic effect is determined to be "strong" or "weak".

A result of determination is shown in Table 1.

Comparative Example 1: Hemostasis of an Incision Site of a Rabbit not Using a Hemostatic Applicator Whether a fluid hemostatic agent flows out of the incision site is verified similarly to Example 2 except that a fluid hemostatic agent is applied to the incision site without using the hemostatic applicator fabricated in Example 1. Based on whether the fluid hemostatic agent flows out, hemostatic effect is determined to be "strong" or "weak". A result of determination is shown in Table 1.

TABLE 1

|  | INCLINED ANGLE | OCCURRENCE OF FLOWING OUT OF FLUIED HEMOSTATIC AGENT | HEMOSTATIC EFFECT |
|---|---|---|---|
| EXAMPLE 2 | 0° | NO | STRONG |
|  | 30° | NO | STRONG |
|  | 60° | NO | STRONG |
| COMPARATIVE EXAMPLE 1 | 0° | NO | STRONG |
|  | 30° | YES | WEAK |
|  | 60° | YES | WEAK |

As shown in Table 1, it can be understood that, when the inclined angle of the incision site is 0°, hemostatic effect of the fluid hemostatic agent is excellent in either Example 2 or Comparative Example 1 irrespective of whether the hemostatic applicator is present. On the other hand, it can be understood that, in a state in which the inclined angle is 30° or 60°, excellent hemostatic effect of the fluid hemostatic agent may be maintained by the hemostatic applicator fabricated in Example 1.

INDUSTRIAL APPLICABILITY

When the bleeding from an incision surface is stopped using a fluid hemostatic agent such as a gelatinous hemostatic agent, a hemostatic agent applicator of the invention may efficiently dispose the fluid hemostatic agent in an affected part of an incision surface irrespective of whether the incision surface is in a horizontal state. Thus, the hemostatic agent applicator of the invention is useful in medical settings relating to surgical procedures, particularly for surface bleeding of a liver or a spleen and internal organ surgery such as fibroid enucleation. An applicator further reduced in size can be applied not only in abdominal surgery, but in endoscopic surgery as well.

REFERENCE SIGN LIST 100, 300, 400, 500, 600: Hemostatic agent applicator
102, 402, 502, 602: Tool body
104, 404, 604: Inlet
106, 406: Wall part
108, 408, 508, 608: Hollow part
110, 410: Open end part
112, 412, 612: Internal pipe
114: End part
116: Connecting part
200: Incision surface
202: Crushed tissue
210: Fluid hemostatic agent
302: Skirt
414: Top
520: Outlet

The invention claimed is:

1. A hemostatic agent applicator for use in disposing a fluid hemostatic agent, comprising:
   a tool body in which a hollow part surrounded by a wall part is formed and which includes an open end part on a downstream side of the wall part, and which includes a top plate on an upstream side of the wall part;
   an inlet provided to be inclined at a predetermined angle on the top plate of the tool body to communicate with the hollow part, and
   a flexible movable member provided in the wall part, wherein:
   the open end part is capable of coming into direct contact with an incision surface formed during surgery such that the tool body covers the incision surface when the open end part comes into direct contact with the incision surface, and
   a diameter of the open end part is longer than a height of the wall part.

2. The hemostatic agent applicator according to claim 1, wherein a distal end of the open end part is provided with a skirt along a circumference direction of the tool body.

3. The hemostatic agent applicator according to claim 1, wherein the inlet is provided with a T shape stopcock.

* * * * *